United States Patent [19]

Diana et al.

[11] Patent Number: 4,575,549

[45] Date of Patent: Mar. 11, 1986

[54] PROCESS FOR THE PREPARATION OF FRUCTOSE 1,6 DIPHOSPHATE ACID

[75] Inventors: Massimo Diana; Guglielmo M. Bisso, both of Rome, Italy

[73] Assignee: Biomedica Foscama Industria Chimico-Farmaceutica S.p.A., Rome, Italy

[21] Appl. No.: 683,254

[22] Filed: Dec. 18, 1984

[30] Foreign Application Priority Data

Dec. 23, 1983 [IT] Italy ............................... 24355 A/83

[51] Int. Cl.$^4$ ............................................... C07H 1/06
[52] U.S. Cl. .................................... 536/117; 536/122; 536/125
[58] Field of Search ....................... 536/117, 125, 122

[56] References Cited

U.S. PATENT DOCUMENTS 3,066,135  11/1962  Baruchello ...................... 536/117
3,684,574  8/1972  Katz et al. ...................... 536/125

Primary Examiner—Johnnie R. Brown
Attorney, Agent, or Firm—Ladas & Parry

[57] ABSTRACT

The process according to the invention provides, for the purification of $FDPH_4$-containing solutions, for a double chromatography combined with the molecular filtration.

There are thus obtained concentrated and highly pure solutions containing fructose 1,6 diphosphate acid, which are perfectly suitable to be employed for the preparation of FDP and its salts.

4 Claims, No Drawings

PROCESS FOR THE PREPARATION OF FRUCTOSE 1,6 DIPHOSPHATE ACID

The present invention provides for a process for preparing on an industrial scale fructose 1,6 diphosphate acid ($FDPH_4$), which is the base reagent used for producing fructose 1,6 diphosphate (FDP) and the relevant isomers.

Fructose 1,6 diphosphate (FDP) is an agent having high glycometabolic activity, widely used in medicine.

In particular, two isomers thereof are employed, namely the fructose 2,6 diphosphate F2, 6P2 and the fructose 1,2 cyclic phosphate 6 phosphate (FDPC).

The preparation on an industrial scale of these two isomers requires very pure and concentrated solutions of fructose 1,6 diphosphate acid ($FDPH_4$), which is the base reagent for such preparations.

The problem that the present invention attempts to solve, therefore, consists in having very pure solutions of $FDPH_4$ available to obtain solutions suitable for preparing the FDP salts in lyophilic powder, and its isomers.

The presently used processes for the industrial production of FDP and the salts thereof comprise:
(a) precipitating FDP as insoluble salt from the liquor of the biological fermentation carried out with yeasts, after interruption with acid;
(b) chromatography by ionic exchange followed by neutralization with alkali to convert the precipitate into salt.

The solutions thus obtained, though, contain many impurities; therefore another purification stage is necessary, which takes place either by salt precipitation (with the inconvenience of employing great quantities of solvent and of separating a strongly hydrated salt), or by lyofilization, which yields, on the other hand, a FDP salt containing impurities in higher degree.

More particularly, the currently used systems for the industrial production of FDP do not allow to directly obtain a sufficiently pure and concentrated $FDPH_4$ solution as to be used as base reagent for the production of FDPC and F 2,6 P2. Up to now these substances were prepared only by laboratory methods using, for the preparation of the $FDPH_4$ solution, complex and expensive methods providing for solving in bidistilled water the FDP sodium salt crystals, and then treating the solution with cation exchange resin, which is subsequently removed by centrifugation.

Several experiments carried out by the Applicant led to a process which allows the industrial production of $FDPH_4$, with a high degree of purity and concentration.

This process needs neither the precipitation in the form of insoluble salt of the FDP produced by biological fermentation, nor the subsequent purification of $FDPH_4$ or of its salt by means of precipitation by crystallization after adding organic solvents to the solutions.

The process according to the invention will be now described in detail, by mere way of non-limiting example.

To put the process into effect there are used solutions of glucose to which inorganic phosphates have been added, solutions which were obtained by biological fermentation with yeasts.

The fermentation liquor is deproteinized by two minutes' pasteurization at 85° C. and then filtered to remove the yeast cells and all the proteins made insoluble after having been denatured by heat. Alternatively, instead of by pasteurization, the deproteinization may be effected by treatment with HCl.

The solution thus prepared is subjected to the following steps:
(a) chromatography with strong cationic resin in order to bring the solution obtained by filtration from the fermentation liquor to a pH inferior to 1;
(b) chromatography with strong anionic resin of the thus obtained acid solution, which fixes $FDPH_4$ and the other phosphate anions, followed by wash of the column with water in order to remove the substances that were not retained by the resin;
(c) elution in three phases with two eluents having increasing ionic strength to remove the inorganic phosphate, part of the phosphorylated carbohydrates (first phase wherein the first eluent is used) and the remaining phosphorylated carbohydrates (second phase wherein 25% of the second eluent is used), and to collect $FDPH_4$ (third phase wherein the remaining part of the second eluent is used);
(d) partial neutralization with NaOH up to pH 3 of the eluate containing the $FDH_4$ collected in the preceding phase;
(e) molecular filtration of the solution obtained by (d) to eliminate NaCl and part of water;
(f) chromatography with strong cationic resin to bring the solution to pH inferior to 1.

The thus obtained solution contains high purity concentrated $FDPH_4$ (up to 20%).

Always for the sake of example, a table is set out hereinafter in which there are listed the characteristics of a salt obtained by lyofilizing the solution, properly neutralized, coming from the working by the known processes (col. 1), compared to the characteristics of a salt obtained by the process according to the invention (col. 2).

|  | I | II |
|---|---|---|
| $FDPH_4$ % | 62.4 | 75.25 |
| $PO_4^=$ % | 5.15 | 0.18 |
| $F6P^=$ % | 0.86 | 0.87 |
| $G6P^=$ % | 0.91 | — |
| $H_2O$ % | 7.77 | 7.88 |
| $Na^+$ % | 14.53 | 15.31 |

The process, therefore, provides for combining the molecular filtration with a cationic chromatography and an anionic chromatography treatment.

By way of information, an example is set out hereunder illustrating the process of the invention.

EXAMPLE 2 lt fermentation liquor is pasteurized for 2' at 85° C., and then filtered on a glass sheet after adding the necessary amount of filtering earth to facilitate the filtering, and then draining the insoluble residue. Thus about 1.5 lt of limpid filtering liquor is obtained, which is let pass through a column containing a strong cationic resin, and then through a second column containing a strong anionic resin.

Operating characteristics

Resins cationic: 200 ml Amberlite IRG 120 form $H^+$ or Duolite C264 form $H^+$;
column: bed h. 500 mm $\phi$ int. 25 mm.

feed speed: 5 ml/min.
anionic: 350 ml Duolite 374 form $Cl^-$
column: bed h. 750 mm $\phi$ int. 25 mm.
elution speed: 20 ml/min.

Once all the liquor has been fed to the cationic column and cascaded over the anionic column, both columns are washed with 400 ml distilled water; then the cascade connection of the two columns is cut out, and the elution of the only anionic column is effected.

The $FDPH_4$ concentration in the feed solution and in the effluent of the anionic column will have been previously determined. An indicative datum is the following:

$FDPH_4$ in the feed solution: 65 gr.
$FDPH_4$ in the effluent after anionic column: 28 gr. (inclusive of wash water).

The elution is carried out in three phases; in the first one about 2.5 lt of a solution containing 1.4 g of $NH_4Cl + 2$ ml of $NH_4$ at 25%/lt is passed; in the second and third phases 2 lt eluent B (ClNa 0.2−HCl 0.05N) is passed, collecting 5 fractions, 2 of 250 ml and the remaining ones of 500 ml. The first and if necessary also the second phases are eliminated, as containing monophosphates carbohydrates and inorganic phosphate (2nd phase), and the other ones are put together obtaining a volume comprised between 1500 and 1750, with a $FDPH_4$ concentration around 2.25–2.5% (3rd phase). This eluate, after neutralization up to pH 43 is subjected to a reverse osmosis process during which the present organic anions and mineral salts—if any—are eliminated, so as to obtain a solution of FDP having a high degree of purity.

Operating characteristics operating pressure 24 atm.
molecular sieve filtering membranes: 500 in cellulose acetate.
filtering surface: mq 1.5

By lyophilizing the solution, which had been properly neutralized with NaOH, a salt is obtained having the analytical characteristics listed in the previous table (I).

However, some variations to the described process may be provided for.

For example, pyridine can be used for neutralizing the eluate. This permits to eliminate the subsequent phase F (chromatography with strong cationic resin) and to obtain a FDP pyridinic salt that can be directly used for producing the two previously cited isomers.

A second variation provides instead for the neutralization of the D phase, effected by KOH. In this way it is possible to eliminate always the F phase and obtain a potassium salt which, if further neutralized with KOH, may be employed in the preparation of the FDP potassium salt or in the form of lyophilic powder.

On the contrary, by stopping the process of the invention at the end of phase E, the resulting solution may be used, upon previous neutralization with NaOH, to obtain the FDP sodium salt in the form of solution or lyophilic powder.

The process according to the invention, thus, allows to obtain industrially 1,6 diphosphate fructose acid, with a yield and a degree of purity that was never obtainable by the known processes.

A person skilled in the art could provide for many changes and variations, which should all fall, however, within the ambit of the present invention.

We claim:

1. A process for the preparation of fructose-1,6-diphosphate starting with the broth obtained after the enzymatic phosphorylation of glucose by brewer's yeast in the presence of inorganic phosphate and comprising the following steps:
    (a) acidification of the broth below pH 2.0 by passage through a strong acid cationic resin
    (b) subsequent passage of the output from the acid column through a strong base anionic resin which retains fructose-1,6-diphosphate and leaves unreacted glucose to be washed out with water
    (c) two-step elution which allows removal of monophosphorylated sugars and inorganic phosphate from fructose-1,6-diphosphate
    (d) partial neutralization of the eluate at pH 3.0
    (e) molecular filtration performed by Reverse Osmosis
    (f) acidification of the resulting solution below pH 1.0 by passage through a strong acid cation resin.

2. A process according to claim 1 wherein the two-step elution in (c) is carried out with a first solution of $NH_4Cl$ 0.56 g/l containing 1% $NH_3$ and then with a second solution of NaCl 0.2M + HCl 0.05N.

3. A process according to claim 1 wherein the neutralization in (d) is carried out with pyridine.

4. A process according to claim 1 wherein the neutralization in (d) is carried out with KOH.

* * * * *